United States Patent
Lee et al.

(10) Patent No.: US 9,818,029 B2
(45) Date of Patent: Nov. 14, 2017

(54) APPARATUS AND METHOD FOR COMPUTER AIDED DIAGNOSIS (CAD) BASED ON EYE MOVEMENT

(71) Applicant: SAMSUNG ELECTRONICS CO., LTD., Suwon-si (KR)

(72) Inventors: Ki Yong Lee, Suwon-si (KR); Byung Kon Kang, Gwangju-si (KR); Keun Joo Kwon, Seoul (KR); Yeong Kyeong Seong, Suwon-si (KR); Seung Woo Ryu, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 37 days.

(21) Appl. No.: 14/965,986

(22) Filed: Dec. 11, 2015

(65) Prior Publication Data

US 2016/0171299 A1  Jun. 16, 2016

(30) Foreign Application Priority Data

Dec. 11, 2014  (KR) ........................ 10-2014-0178733

(51) Int. Cl.
| | |
|---|---|
| *G06K 9/00* | (2006.01) |
| *G06F 19/00* | (2011.01) |
| *A61B 3/113* | (2006.01) |
| *A61B 8/10* | (2006.01) |
| *A61B 8/00* | (2006.01) |
| *A61B 8/08* | (2006.01) |

(52) U.S. Cl.
CPC .......... *G06K 9/00604* (2013.01); *A61B 3/113* (2013.01); *A61B 8/10* (2013.01); *A61B 8/469* (2013.01); *A61B 8/5223* (2013.01); *G06F 19/345* (2013.01); *A61B 8/08* (2013.01); *A61B 2576/00* (2013.01)

(58) Field of Classification Search
None
See application file for complete search history.

(56) References Cited

U.S. PATENT DOCUMENTS

| | | | | |
|---|---|---|---|---|
| 5,731,805 | A * | 3/1998 | Tognazzini | G06F 3/013 345/156 |
| 7,331,929 | B2 | 2/2008 | Morita et al. | |
| 7,396,129 | B2 * | 7/2008 | Endrikhovski | G06F 3/038 345/619 |
| 8,098,910 | B2 * | 1/2012 | Srinivasan | A61B 8/06 382/128 |
| 8,295,541 | B2 * | 10/2012 | Naylor | G08B 13/1961 382/103 |
| 8,564,533 | B2 | 10/2013 | Yuan | |
| 9,095,283 | B1 * | 8/2015 | Guez | A44C 5/20 |

(Continued)

FOREIGN PATENT DOCUMENTS

JP        5077879 B2    11/2012

*Primary Examiner* — Avinash Yentrapati
(74) *Attorney, Agent, or Firm* — Sughrue Mion, PLLC (57) ABSTRACT

An apparatus and a method for Computer Aid Diagnosis (CAD) based on eye movement are provided. The apparatus includes a gaze area detector configured to detect, based on eye movement of a user, a gaze area on a medical image on which a region of interest (ROI) is detected, the gaze area being an area at which the user gazes for a period of time. The apparatus further includes an ROI redetector configured to detect another ROI on the gaze area.

16 Claims, 7 Drawing Sheets

(56) References Cited

U.S. PATENT DOCUMENTS

| | | | | |
|---|---|---|---|---|
| 2001/0031076 A1* | 10/2001 | Campanini | G06F 19/345 | 382/128 |
| 2003/0095697 A1* | 5/2003 | Wood | A61B 6/032 | 382/131 |
| 2003/0122942 A1* | 7/2003 | Parker | H04N 19/176 | 348/231.3 |
| 2006/0082542 A1* | 4/2006 | Morita | A61B 5/7475 | 345/156 |
| 2006/0112334 A1* | 5/2006 | Endrikhovski | G06F 3/013 | 715/700 |
| 2008/0062382 A1* | 3/2008 | Endrikhovski | G06F 3/013 | 351/209 |
| 2008/0113317 A1* | 5/2008 | Kemp | G06T 7/0012 | 433/215 |
| 2008/0298662 A1* | 12/2008 | Periaswamy | G06T 7/0012 | 382/131 |
| 2009/0123025 A1* | 5/2009 | Deng | G06K 9/00711 | 382/100 |
| 2009/0146950 A1* | 6/2009 | Maringelli | G06F 19/3406 | 345/158 |
| 2009/0245600 A1* | 10/2009 | Hoffman | A61B 1/00039 | 382/128 |
| 2010/0131887 A1* | 5/2010 | Salazar-Ferrer | G06F 3/0481 | 715/788 |
| 2010/0226564 A1* | 9/2010 | Marchesotti | G06F 17/30256 | 382/159 |
| 2010/0246884 A1* | 9/2010 | Chen | G06T 7/0012 | 382/103 |
| 2010/0316279 A1* | 12/2010 | Meetz | A61B 6/504 | 382/131 |
| 2011/0006978 A1* | 1/2011 | Yuan | G06F 3/013 | 345/156 |
| 2011/0029918 A1* | 2/2011 | Yoo | G06F 3/017 | 715/800 |
| 2011/0087659 A1* | 4/2011 | Dey | G06F 17/30696 | 707/728 |
| 2011/0103673 A1* | 5/2011 | Rosenstengel | G06T 7/0012 | 382/132 |
| 2011/0270123 A1* | 11/2011 | Reiner | A61B 6/463 | 600/558 |
| 2012/0051606 A1* | 3/2012 | Saikia | G06T 7/62 | 382/128 |
| 2012/0187312 A1* | 7/2012 | Guez | A44C 5/20 | 250/492.1 |
| 2012/0257791 A1* | 10/2012 | Woo | G06T 7/13 | 382/103 |
| 2013/0058523 A1* | 3/2013 | Wu | G06K 9/00785 | 382/103 |
| 2013/0271454 A1* | 10/2013 | Lyons | G06T 11/60 | 345/419 |
| 2013/0272587 A1* | 10/2013 | Fang | G06F 19/321 | 382/128 |
| 2014/0168056 A1* | 6/2014 | Swaminathan | G06K 9/00604 | 345/156 |
| 2014/0354689 A1* | 12/2014 | Lee | A61B 1/00045 | 345/633 |
| 2015/0080735 A1* | 3/2015 | Hyun | A61B 8/06 | 600/454 |
| 2015/0287186 A1* | 10/2015 | Holzhacker | A61B 5/0536 | 382/131 |
| 2015/0302583 A1* | 10/2015 | Jeon | G06T 7/0016 | 382/128 |
| 2016/0042525 A1* | 2/2016 | Lee | G06K 9/00208 | 382/103 |
| 2016/0110875 A1* | 4/2016 | Sugiyama | A61B 8/0825 | 382/131 |

* cited by examiner

APPARATUS AND METHOD FOR COMPUTER AIDED DIAGNOSIS (CAD) BASED ON EYE MOVEMENT

CROSS-REFERENCE TO RELATED APPLICATION

This application claims priority from Korean Patent Application No. 10-2014-0178733, filed on Dec. 11, 2014, in the Korean Intellectual Property Office, the disclosure of which is incorporated herein by reference in its entirety.

BACKGROUND

1. Field

Apparatuses and methods consistent with exemplary embodiments relate to Computer Aided Diagnosis (CAD) technology, and more particularly, to an apparatus and a method for CAD based on eye movement.

2. Description of the Related Art

A Computer Aided Diagnosis (CAD) system is a system that analyzes medical images, i.e., ultrasonic images, and displays a suspicious area on a medical image according to a diagnostic result to help a doctor to diagnose a patient's disease. It is almost impossible for humans to perform diagnosis without any error because of their limited perceptive capability. In addition, great attention and care may be used to analyze each medical image. The CAD system can help solve these drawbacks by helping raise accuracy of diagnosis and alleviating the burden of doctors.

The CAD system detects a region of interest (ROI) from each image frame, and displays the detection result. In this case, a false positive or false negative result for an ROI may dampen a user's satisfaction.

Therefore, there is a need for a technology for receiving a user's feedback on a false positive or false negative result for an ROI to improve accuracy of the detection.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

According to an aspect of an exemplary embodiment, there is provided a Computer Aided Diagnosis (CAD) apparatus including a gaze area detector configured to detect, based on eye movement of a user, a gaze area on a medical image on which a region of interest (ROI) is detected, the gaze area being an area at which the user gazes for a period of time. The apparatus further includes an ROI redetector configured to detect another ROI on the gaze area.

The ROI redetector may be further configured to detect the other ROI on the gaze area, using a lesion detection model that is different from another lesion detection model that is used in the detection of the ROI on the medical image.

The CAD apparatus may further include an additional image acquirer configured to acquire one or more additional images of the gaze area by adjusting parameters or a frame rate of a probe that is used to acquire the medical image or by transforming a portion where the gaze area is positioned in the medical image. The ROI redetector may be further configured to detect an ROI on each of the one or more additional images.

The parameters of the probe may include at least one among a frequency, a bandwidth, a power intensity, a gain, and a depth of focus of an ultrasonic signal.

The additional image acquirer may be further configured to transform the portion where the gaze area is positioned in the medical image, using at least one among Horizontal Flip, Rotation, Cropping, Scaling, Shearing, Jittering, Stretching, Blurring, Sharpening, Histogram Modification, Restoration, and Noise addition.

The CAD apparatus may further include a classifier configured to classify the other ROI on the gaze area.

The CAD apparatus may further include an ROI detector configured to detect the ROI on the medical image.

The CAD apparatus may further include a display configured to display the ROI on the medical image.

The display may be further configured to modify the ROI on the medical image based on the other ROI on the gaze area.

The display may be further configured to determine whether an ROI on the medical image with respect to the gaze area is one among a false positive, a false negative, and a true positive, based on the other ROI on the gaze area, in response to the display determining that the ROI on the medical image with respect to the gaze area is the false positive, remove a marker for the ROI on the medical image with respect to the gaze area, in response to the display determining that the ROI on the medical image with respect to the gaze area is the false negative, add the marker for the ROI on the medical image with respect to the gaze area, and in response to the display determining that the ROI on the medical image with respect to the gaze area is the true positive, maintain the marker for the ROI on the medical image with respect to the gaze area.

According to an aspect of another exemplary embodiment, there is provided a Computer Aided Diagnosis (CAD) method including detecting, based on eye movement of a user, a gaze area on a medical image on which a region of interest (ROI) is detected, the gaze area being an area at which the user gazes for a period of time, and detecting another ROI on the gaze area.

The detecting the other ROI on the gaze area may include detecting the other ROI on the gaze area, using a lesion detection model that is different from another lesion detection model that is used in the detection of the ROI on the medical image.

The CAD method may further include acquiring one or more additional images of the gaze area by adjusting parameters or a frame rate of a probe that is used to acquire the medical image or by transforming a portion where the gaze area is positioned in the medical image. The detecting the other ROI on the gaze area may include detecting an ROI on each of the one or more additional images.

The acquiring may include transforming the portion where the gaze area is positioned in the medical image, using at least one among Horizontal Flip, Rotation, Cropping, Scaling, Shearing, Jittering, Stretching, Blurring, Sharpening, Histogram Modification, Restoration, and Noise addition.

The CAD method may further include classifying the other ROI on the gaze area.

The CAD method may further include detecting the ROI on the medical image.

The CAD method may further include displaying the ROI on the medical image.

The CAD method may further include modifying the ROI on the medical image based on the other ROI on the gaze area.

The modifying may include determining whether an ROI on the medical image with respect to the gaze area is one among a false positive, a false negative, and a true positive, based on the other ROI on the gaze area, in response to the determining that the ROI on the medical image with respect to the gaze area is the false positive, removing a marker for the ROI on the medical image with respect to the gaze area, in response to the determining that the ROI on the medical image with respect to the gaze area is the false negative, adding the marker for the ROI on the medical image with respect to the gaze area, and in response to the determining that the ROI on the medical image with respect to the gaze area is the true positive, maintaining the marker for the ROI on the medical image with respect to the gaze area.

BRIEF DESCRIPTION OF THE DRAWINGS

The above and/or other aspects will become more apparent by describing exemplary embodiments with reference to the accompanying drawings, in which.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail because they would obscure the description with unnecessary detail.

Figure 1:
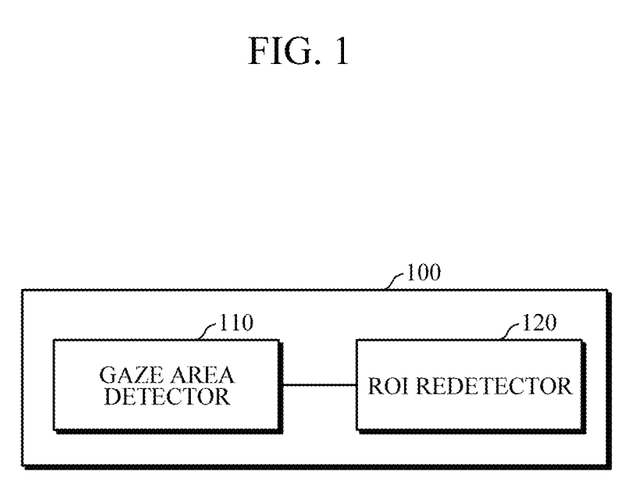
FIG. 1 is a diagram illustrating an apparatus for Computer Aided Diagnosis (CAD) based on eye movement, according to an exemplary embodiment.

FIG. 1 is a diagram illustrating an apparatus 100 for Computer Aided Diagnosis (CAD) based on eye movement, according to an exemplary embodiment. Referring to FIG. 1, the apparatus 100 for CAD includes a gaze area detector 110 and a region of interest (ROI) redetector 120.

The gaze area detector 110 detects eye movement of a user. Then, based on the eye movement, the gaze area detector 110 detects an area gazed by the user from a medical image on which a primary detection of an ROI is completed. The ROI may include not only a malignant lesion area but also a lesion area that is indefinite as to malignancy/benignancy and an area with unique characteristics. In addition, the medical image may be an ultrasonic image that is acquired in real time by a probe on a frame unit basis.

According to an exemplary embodiment, based on eye movement of a user, the gaze area detector 110 may determine whether the user gazes, for a predetermined threshold period of time, at an area in a medical image from which a primary detection of an ROI is completed. Then, the gaze area detector 100 may determine the area in the medical image to be a gaze area.

The threshold period of time is a value set by a user. A threshold period of time may be set differently according to a user, or may be set as a fixed value regardless of who is a user. In addition, the threshold period of time may be learned and updated adaptively. Time in which the user gazes at the area may be continuous or intermittent.

The gaze area detector 110 may detect eye movement of a user in various ways. For example, to sense eye movement of a user, the gaze area detector 110 may use an assistant device, such as glasses with an embedded camera or a monitor with an embedded camera. However, the above is an example, and aspects of the present disclosure are not limited thereto.

The ROI redetector 120 secondarily detects an ROI from a gaze area detected by the gaze area detector 110.

According to an exemplary embodiment, the ROI redetector 120 may secondarily detect an ROI from a gaze area, using a lesion detection model that is different from a lesion detection model used in the primary detection. For example, if Deformable Part Models (DPM) are used in the primary detection, the ROI redetector 120 may secondarily detect an ROI from a gaze area, using a Convolutional Neural Network (CNN) that is different from DPM. In another example, if the CNN is used in the primary detection, the ROI redetector 120 may secondarily detect an ROI from a gaze area, using a lesion detection model that has the same type but is learned in a different way compared to CNN (e.g., CNN that has been learned with respect to an image portion of the entire image).

According to another exemplary embodiment, the ROI redetector 120 may adjust parameters of a lesion detection model used in the primary detection of an ROI, and secondarily detect an ROI from a gaze area, using the lesion detection model applied with the adjusted parameters. That is, based on eye movement of a user, the apparatus 100 may detect a gaze area from an acquired real-time medical image on which detection of an ROI is completed, and then the apparatus 100 may secondarily detect an ROI from the gaze area. In this manner, accuracy of detection of an ROI may improve.

Figure 2:
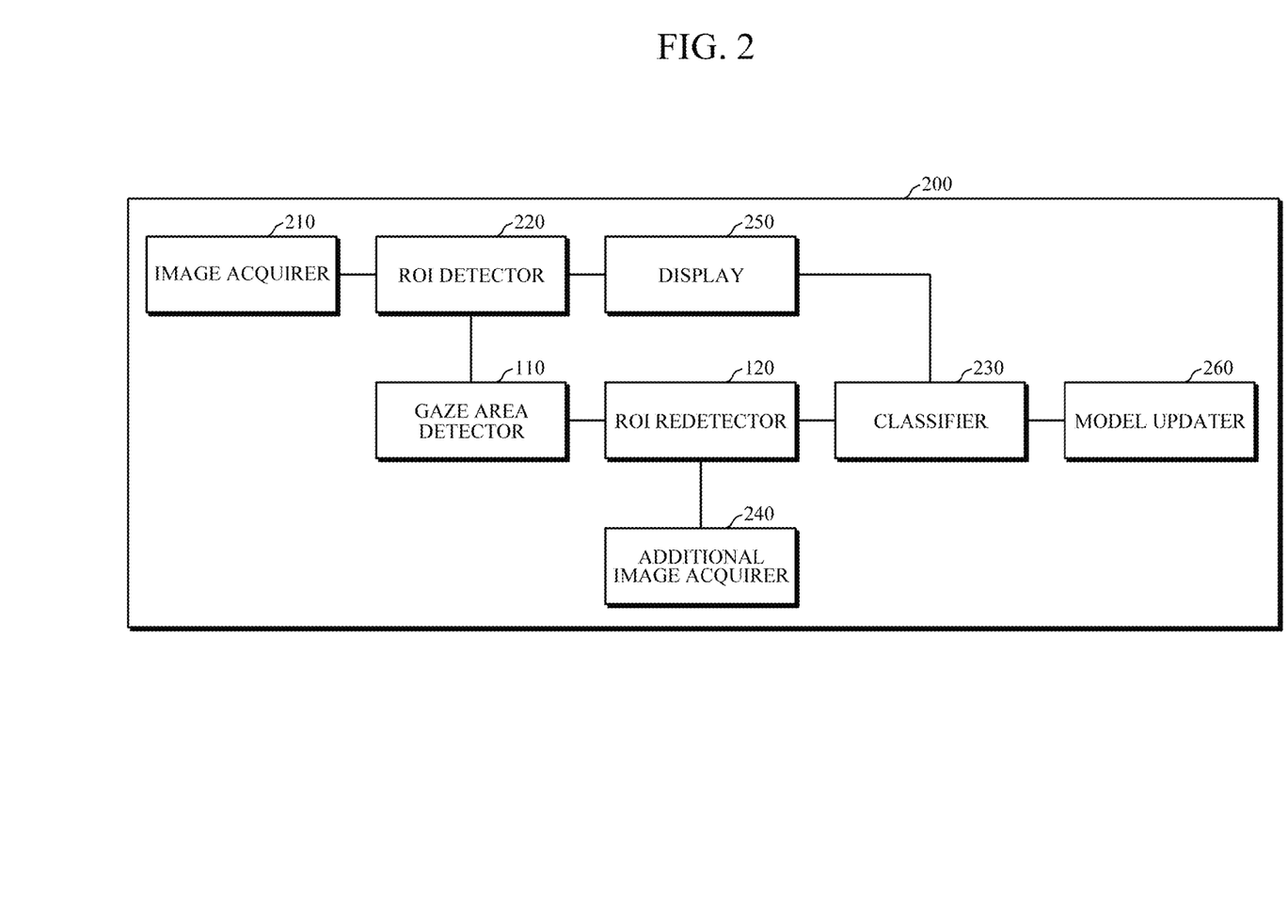
FIG. 2 is a diagram illustrating an apparatus for CAD based on eye movement, according to another exemplary embodiment.

FIG. 2 is a diagram illustrating an apparatus 200 for CAD based on eye movement, according to another exemplary embodiment. Referring to FIG. 2, the CAD apparatus 200 includes an image acquirer 210, a ROI detector 220, a classifier 230, an additional image acquirer 240, a display 250, and a model updater 260 in addition to the gaze area detector 110 and the ROI detector 120.

The image acquirer 210 acquires a medical image of a patient. The medical image may be an ultrasonic image that is acquired through a probe in real time on a frame unit basis.

The ROI detector 220 analyzes a medical image acquired in real time by the image acquirer 210, and primarily detects an ROI from the medical image. The ROI may include not only a malignant lesion area but also a lesion area that is indefinite as to malignancy/benignancy or an area having unique characteristics.

According to an exemplary embodiment, the ROI detector 220 may primarily detect an ROI from an image frame, using a lesion detection algorithm. The lesion detection algorithm may include AdaBoost, DPM, Deep Neural Network (DNN), CNN, Sparse Coding, and the like. However, the above are examples, and aspects of the present disclosure are not limited thereto.

The classifier 230 classifies an ROI detected from a gaze area. According to an exemplary embodiment, the classifier 230 may determine whether an ROI detected from a gaze area is malignant or benign, using a lesion classification algorithm. The lesion classification algorithm may include Support Vector Machine (SVM), Decision Tree, Deep Belief Network (DBN), CNN, and the like, but aspects of the present disclosure are not limited thereto.

The additional image acquirer 240 acquires an additional image of a gaze area. According to an exemplary embodiment, the additional image acquirer 240 may acquire one or more additional images of a gaze area by adjusting parameters of a probe used to acquire a medical image. The parameters of a probe may include frequency, bandwidth, power intensity, depth of focus, and gain of an ultrasonic signal. However, the above are examples, and aspects of the present disclosure are not limited thereto.

According to another exemplary embodiment, the additional image acquirer 240 may acquire one or more additional images of a gaze area by adjusting a frame rate.

According to yet another exemplary embodiment, the additional image acquirer 240 may acquire one or more additional images of a gaze area by transforming a portion where the gaze area is positioned in a medical image. The additional image acquirer 240 may transform a portion where a gaze area is positioned in a medical image, by using Horizontal Flip, Rotation, Cropping, Scaling, Shearing, Jittering, Stretching, Blurring, Sharpening, Histogram Modification, Restoration, Noise addition, and the like. However, the above are examples and aspects of the present disclosure are not limited, and other various image transforming techniques may be used.

In this case, the ROI redetector 120 may detect an ROI from each additional image acquired by the additional image acquirer 240. Then, the classifier 230 may classify an ROI in each additional image, and compute a classification result of an ROI detected from a gaze area by combining classification results of all the ROIs in the additional images. For example, the classifier 230 may compute a classification result of a ROI detected from a gaze area by applying a voting algorithm to all classification results of the all the ROIs in the additional images.

The display 250 displays, on a screen, a primary detection result of an ROI in a medical image. According to an exemplary embodiment, the display 250 may indicate a location of an ROI detected by the ROI detector 220 by covering the ROI with a bounding box or by marking a dot or a cross at the center of the ROI. However, aspects of the present disclosure are not limited thereto, and the display 250 may display the ROI in various ways. For example, the display 250 may display an ROI with various kinds of distinguished markers, such as a circle and a triangle, or using various kinds of color.

Based on the secondary detection result obtained by the ROI redetector 120 and/or a classification result obtained by the classifier 230, the display 250 may modify the primary detection result of an ROI. In an exemplary embodiment, if, based on the secondary detection result obtained by the ROI redetector 120 and/or a classification result obtained by the classifier 230, the primary detection result of the ROI with respect to the gaze area is determined to be a false positive, the display 250 may remove a marker for the ROI with respect to the gaze area. For example, if an ROI is detected primarily but not detected secondarily from a gaze area or where an ROI is primarily and secondarily detected from a gaze area and a classification result thereof is benign, the display 250 may determine a primary detection result of the ROI with respect to the gaze area to be a false positive, and remove a marker for the ROI with respect to the gaze area.

In another exemplary embodiment, if, based on the secondary detection result obtained by the ROI redetector 120 and/or a classification result obtained by the classifier 230, a primary detection result of an ROI with respect to the gaze area is determined to be a false negative, the display 250 may add a marker for the ROI with respect to the gaze area. For example, if an ROI is not detected primarily but detected secondarily from a gaze area, the display 250 may determine a primary detection result of the ROI with respect to the gaze area to be a false negative, and add a marker for the ROI with respect to the gaze area.

In yet another exemplary embodiment, if, based on the secondary detection result obtained by the ROI redetector 120 and/or a classification result obtained by the classifier 230, a primary detection result of an ROI with respect to a gaze area is determined to be a true positive, the display 250 may maintain a marker for the ROI with respect to the gaze area. For example, if an ROI is primarily and secondarily detected from a gaze area, the display 250 may determine a primary detection result of the ROI with respect to the gaze area to be a true positive, and maintain a marker for the ROI with respect to the gaze area.

Based on the secondary detection result obtained by the ROI redetector 120 and/or a classification result obtained by the classifier 230, the model updater 260 updates a lesion detection model to be used by the ROI detector 220.

Hereinafter, one or more exemplary embodiments in which a CAD apparatus is applied are described with reference to FIGS. 3, 4, and 5. In the following description about FIGS. 3, 4, and 5, it is assumed that a medical image acquired in real time is displayed on a screen simultaneously with a primary detection result of an ROI.

Figure 3:
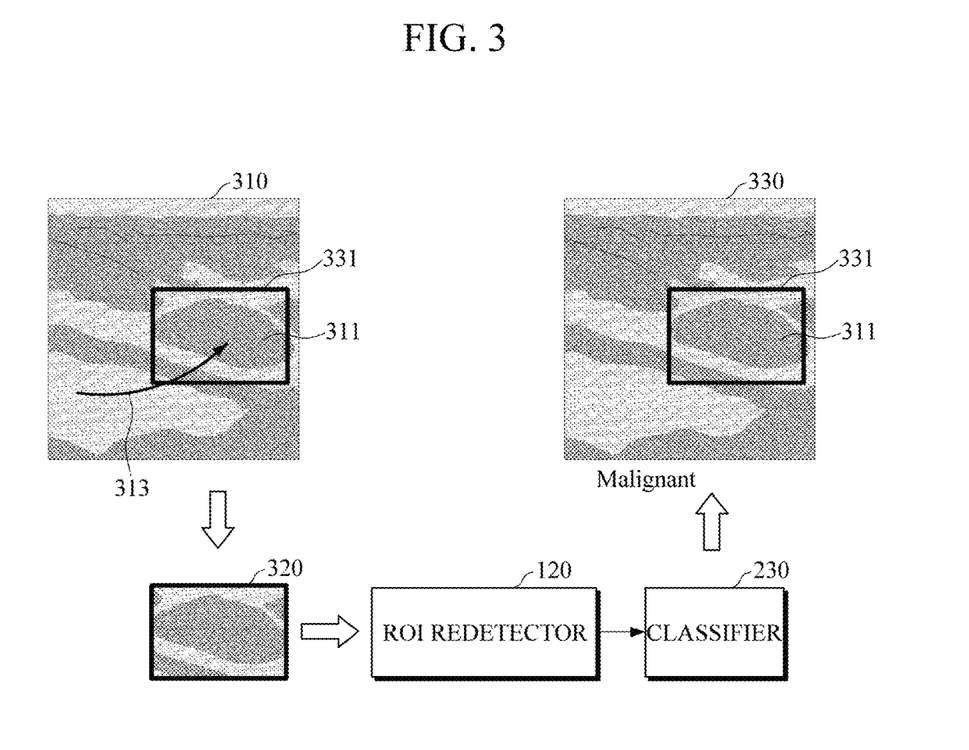
FIG. 3 is a diagram illustrating a primary detection result of an ROI being a true positive, according to an exemplary embodiment.

FIG. 3 is a diagram illustrating a primary detection result of an ROI 311 being a true positive, according to an exemplary embodiment. Referring to FIG. 3, the ROI detector 220 primarily detects the ROI 311 from a medical image 310 that is acquired in real time, and the display 250 displays, on a screen, a distinguished marker 331 for the ROI 311 in the medical image 310.

The gaze area detector 110 senses eye movement 313 of a user. Then, if the user gazes at the ROI 311 for a threshold period of time, the gaze area detector 110 detects the ROI 311 as a gaze area 320.

The ROI redetector 120 secondarily detects an ROI from the gaze area 320, using a lesion detection model that is different from a lesion detection model that is used in a primary detection of an ROI.

The classifier 230 classifies the ROI detected from the gaze area 320, and determines that the ROI detected from the gaze area 320 is malignant.

The display 250 determines that a primary detection result of the ROI 311 with respect to the gaze area 320 is a true positive, and maintains the distinguished marker 331 for the ROI 311 with respect to the gaze area 320 in the medical image 330 that is currently displayed on the screen.

Figure 4:
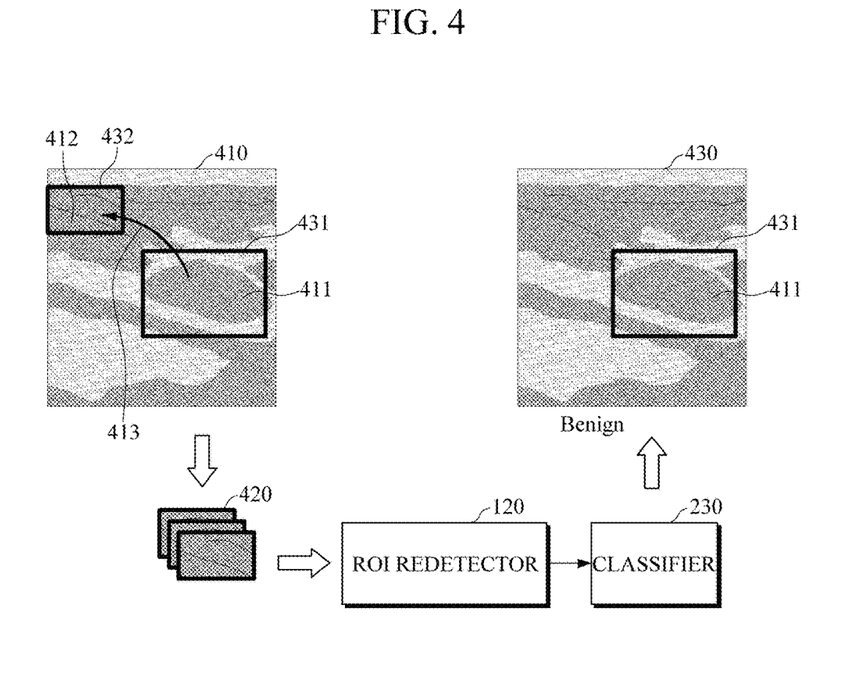
FIG. 4 is a diagram illustrating a primary detection result of an ROI being a false positive, according to an exemplary embodiment.

FIG. 4 is a diagram illustrating a primary detection result of an ROI being a false positive, according to an exemplary embodiment. Referring to FIG. 4, the ROI detector 220 primarily detects an ROI 1 411 and an ROI 2 412 from a medical image 410 that is acquired in real time, and the display 250 displays, on a screen, distinguished markers 431 and 432 for the ROI 1 411 and the ROI 2 412, respectively, in the medical image 410.

The gaze area detector 110 senses eye movement 413 of a user. Then, if the user gazes at the ROI 412 for a threshold period of time, the gaze area detector 110 detects the ROI 2 412 as a gaze area.

The additional image acquirer 240 acquires one or more additional images 420 of the ROI 2 412 by adjusting parameters or a frame rate of a probe.

The ROI redetector 120 secondarily detects an ROI from each of the additional images 420. For the secondary detection, the ROI redetector 120 may use a lesion detection model that is used in the primary detection, or may use a lesion detection model that is different from the lesion detection model used in the primary detection.

The classifier 230 classifies an ROI in each of the additional images 420, combines all results of the classifications of all the ROIs in the additional images, and determines that the ROI 2 412 is benign.

The display 250 determines that a primary detection result of the ROI 2 412 with respect to the gaze area is a false positive, and removes the distinguished marker 432 for the ROI 2 412 from the medical image 430 that is currently displayed on the screen.

Figure 5:
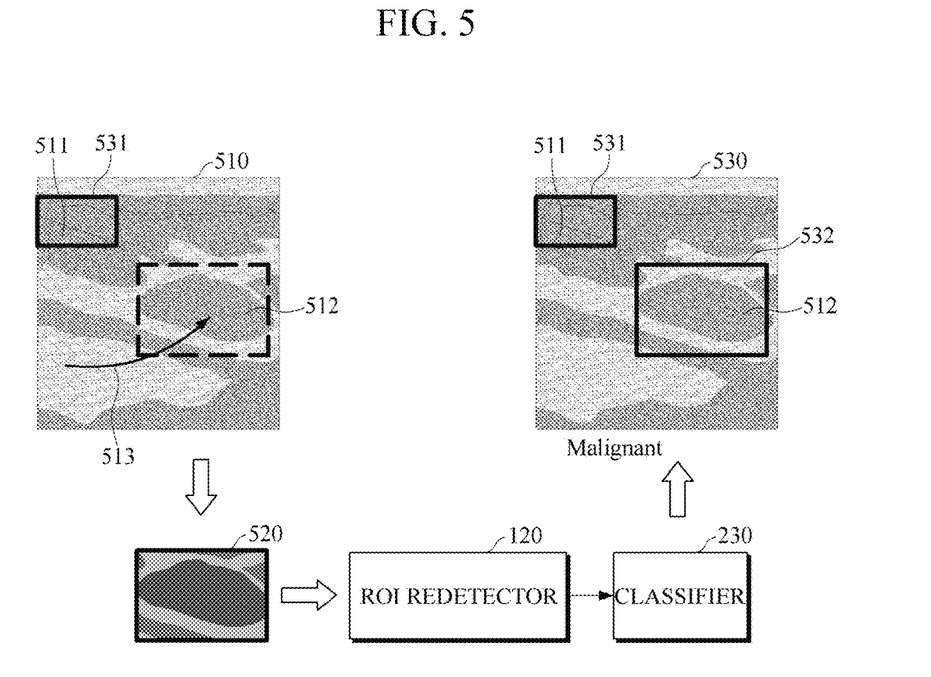
FIG. 5 is a diagram illustrating a primary detection result of an ROI being a false negative, according to an exemplary embodiment.

FIG. 5 is a diagram illustrating a primary detection result of an ROI being a false negative, according to an exemplary embodiment. Referring to FIG. 5, the ROI detector 220 primarily detects an ROI 511 from a medical image 510 that is acquired in real time, and the display 250 displays, on a screen, a distinguished marker 531 for the ROI 511 in the medical image 510.

The gaze area detector 110 senses eye movement 513 of a user. Then, if the user gazes at an area 512 in the medical image 510 for a threshold period of time, the gaze area detector 110 detects the area 512 as a gaze area.

The additional image acquirer 240 acquires an additional image 520 of the area 512 by transforming the area 512 in the medical image 510.

The ROI redetector 120 secondarily detects an ROI from the additional image 520. For the detection, the ROI redetector 120 may use a lesion detection model that is used in the primary detection, or may use a lesion detection model different from the lesion detection model used in the primary detection.

The classifier 230 classifies the ROI in the additional image 520, and determines that the area 512 is malignant based on a result of the classification.

The display 250 determines a primary detection result of the ROI with respect to the gaze area to be a false negative, and adds a distinguished marker 532 for the ROI with respect to the area 512 corresponding to the gaze area to the medical image 530 that is currently displayed on the screen.

Figure 6:
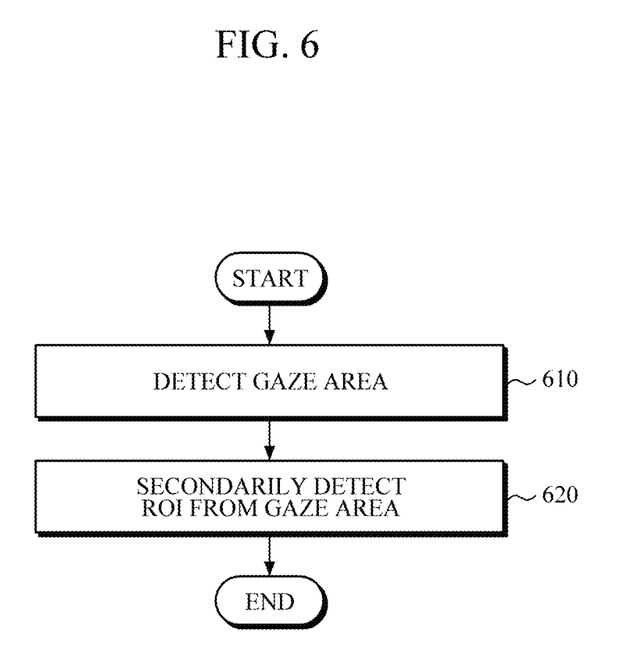
FIG. 6 is a flowchart illustrating a method for CAD based on eye movement, according to an exemplary embodiment.

FIG. 6 is a flowchart illustrating a method for CAD based on eye movement, according to an exemplary embodiment. FIG. 6 is described with reference to FIG. 1.

Referring to FIG. 6, in operation 610, in a CAD method according to an exemplary embodiment, a gaze area of a user is detected, based on eye movement of the user, from an image on which primary detection of an ROI is completed. For example, the apparatus 100 may sense eye movement of the user, and, based on the eye movement, detect the user's gaze area from a medical image on which primary detection of an ROI is completed.

In operation 620, an ROI is secondarily detected from the gaze area. For example, for the secondary detection, the apparatus 100 may adjust parameters of a lesion detection model that is used in the primary detection, and apply the lesion detection model with the adjusted parameters. In another example, for the secondary detection, the apparatus 100 may apply a lesion detection model that is different from the lesion detection model used in the primary detection. In this case, the lesion detection model different from the lesion detection model used in the primary detection may be a lesion detection model of a different type from that of the lesion detection model used in the primary detection, or may be a lesion detection model that has the same type but has been learned in different way compared to the lesion detection model used in the primary detection.

Figure 7:
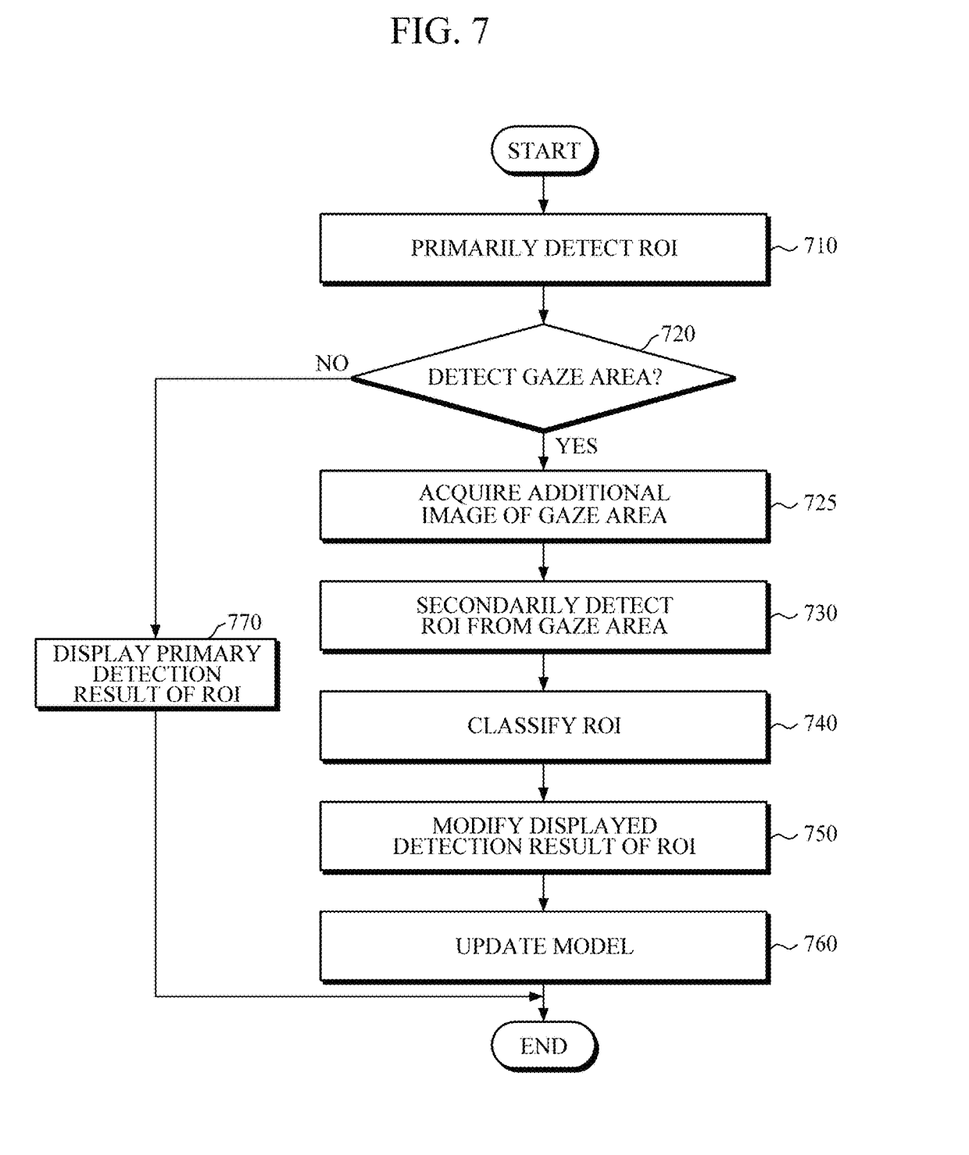
FIG. 7 is a flowchart illustrating a method for CAD based on eye movement, according to another exemplary embodiment.

FIG. 7 is a flowchart illustrating a method for CAD based on eye movement, according to another exemplary embodiment. FIG. 7 is described with reference to FIG. 2.

Referring to FIG. 7, in operation 710, in a CAD method according to another exemplary embodiment, the apparatus 200 primary detects an ROI from a medical image that is acquired in real time. For example, the apparatus 200 may primarily detect an ROI from an image frame, using a lesion detection algorithm. The lesion detection algorithm may include AdaBoost, Deformable Part Models (DPM), Deep Neural Network (DNN), Convolutional Neural Network (CNN), Sparse Coding, and the like. However, the above is an example, and aspects of the present disclosure are not limited thereto.

In operation 720, based on eye movement of the user, the apparatus 200 determines whether a user's gaze area is detected from the image where the primary detection of the ROI is completed. If the apparatus 200 determines that the user's gaze is detected, the apparatus 200 continues in operation 725. Otherwise, the apparatus 200 continues in operation 770.

In operation 725, the apparatus 200 may acquire at least one additional image of the gaze area.

In operation 730, the apparatus 200 secondarily detects an ROI from the gaze area or the additional image.

In operation 740, the apparatus 200 classifies the ROI detected from the gaze area. For example, using a lesion classification algorithm, the apparatus 200 may determine whether the ROI detected from the gaze area is malignant or benign. The lesion classification algorithm may include Support Vector Machine (SVM), Decision Tree, Deep Belief Network (DBN), Convolutional Neural Network (CNN), and the like. However, the above are examples, and aspects of the present disclosure are not limited thereto.

In operation 750, based on a secondary detection result and/or classification result of the ROI with respect to the gaze area, the apparatus 200 modifies a primary detection result that is displayed on a screen. For example, if a determination that is made based on a secondary detection result and/or classification result of the ROI with respect to the gaze area, is that the primary detection result of the ROI with respect to the gaze area is a false positive, the apparatus 200 may remove a distinguished marker for the ROI with respect to the gaze area on the screen.

In another example, if a determination that is made based on a secondary detection result and/or classification result of the ROI with respect to the gaze area, is that the primary detection result of the ROI with respect to the gaze area is a false negative, the apparatus 200 may add, on the screen, a distinguished maker for the ROI with respect to the gaze area.

In yet another example, if a determination that is made based on a secondary detection result and/or classification result of the ROI with respect to the gaze area, is that the primary detection result of the ROI with respect to the gaze area is determined to be a true positive, the apparatus 200 may maintain, on the screen, a distinguished marker for the ROI with respect to the gaze area.

In operation 760, based on the secondary detection result and/or classification result of the ROI with respect to the gaze area, the apparatus 200 updates a lesion detection model that is used in the primary detection.

In operation 770, the apparatus 200 displays the primary detection result of the ROI on the screen.

According to another exemplary embodiment, the apparatus 200 may acquire one or more additional images of a gaze area by adjusting parameters or a frame rate of a probe that is used to acquire a medical image or by transforming a portion where the gaze area is positioned in a medical image. In this case, the apparatus 200 secondarily detects an ROI from each additional image in operation 730, classifies an ROI in each additional image in operation 740, and compute a classification result of an ROI that is detected from the gaze area by combining all classification results of ROIs in the additional images.

While not restricted thereto, an exemplary embodiment can be embodied as computer-readable code on a computer-readable recording medium. For example, a control program that controls the above-described operations may be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units can include circuitry, a processor, a microprocessor, etc., and may execute a computer program stored in a computer-readable medium.

The foregoing exemplary embodiments and advantages are examples and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A Computer Aided Diagnosis (CAD) apparatus comprising:
    a memory configured to store instructions therein; and
    at least one processor, upon execution of the instructions, configured to:
        detect at least one region of interest (ROI) on a medical image;
        detect, based on eye movement of a user, a gaze area on the medical image on which the at least one ROI on the medical image is detected, the gaze area being an area at which the user gazes for a period of time;
        detect at least one ROI on the gaze area; and
        modify a first detection result of the at least one ROI on the medical image, based on a second detection result of the at least one ROI on the gaze area.

2. The CAD apparatus of claim 1, wherein the at least one processor is further configured to detect the at least one ROI on the gaze area, using a lesion detection model that is different from another lesion detection model that is used in the detection of the at least one ROI on the medical image.

3. The CAD apparatus of claim 1, wherein the at least one processor is further configured to:
    acquire one or more additional images of the gaze area by adjusting parameters or a frame rate of a probe that is used to acquire the medical image or by transforming a portion where the gaze area is positioned in the medical image; and
    detect at least one ROI on each of the one or more additional images.

4. The CAD apparatus of claim 3, wherein the parameters of the probe comprise at least one among a frequency, a bandwidth, a power intensity, a gain, and a depth of focus of an ultrasonic signal.

5. The CAD apparatus of claim 3, wherein the at least one processor is further configured to transform the portion where the gaze area is positioned in the medical image, using at least one among Horizontal Flip, Rotation, Cropping, Scaling, Shearing, Jittering, Stretching, Blurring, Sharpening, Histogram Modification, Restoration, and Noise addition.

6. The CAD apparatus of claim 1, wherein the at least one processor is further configured to classify the at least one ROI on the gaze area.

7. The CAD apparatus of claim 1, further comprising:
    a display configured to display the modified first detection result of the at least one ROI on the medical image.

8. The CAD apparatus of claim 1, wherein the at least one processor is further configured to:
    determine whether an ROI on the medical image with respect to the gaze area is one among a false positive, a false negative, and a true positive, based on the at least one ROI on the gaze area;
    in response to the determining that the at least one ROI on the medical image with respect to the gaze area is the false positive, remove a marker for the at least one ROI on the medical image with respect to the gaze area;
    in response to the determining that the at least one ROI on the medical image with respect to the gaze area is the false negative, add the marker for the at least one ROI on the medical image with respect to the gaze area; and
    in response to the determining that the at least one ROI on the medical image with respect to the gaze area is the true positive, maintain the marker for the at least one ROI on the medical image with respect to the gaze area.

9. A Computer Aided Diagnosis (CAD) method comprising:
    detecting at least one region of interest (ROI) on a medical image;
    detecting, based on eye movement of a user, a gaze area on the medical image on which the at least one ROI on the medical image is detected, the gaze area being an area at which the user gazes for a period of time;
    detecting at least one ROI on the gaze area; and
    modifying a first detection result of the at least one ROI on the medical image based on a second detection result of the at least one ROI on the gaze area.

10. The CAD method of claim 9, wherein the detecting the at least one ROI on the gaze area comprises detecting the at least one ROI on the gaze area, using a lesion detection model that is different from another lesion detection model that is used in the detection of the at least one ROI on the medical image.

11. The CAD method of claim 9, further comprising:
acquiring one or more additional images of the gaze area by adjusting parameters or a frame rate of a probe that is used to acquire the medical image or by transforming a portion where the gaze area is positioned in the medical image,
wherein the detecting the at least one ROI on the gaze area comprises detecting at least one ROI on each of the one or more additional images.

12. The CAD method of claim 11, wherein the parameters of the probe comprise at least one among a frequency, a bandwidth, a power intensity, a gain, and a depth of focus of an ultrasonic signal.

13. The CAD method of claim 11, wherein the acquiring comprises transforming the portion where the gaze area is positioned in the medical image, using at least one among Horizontal Flip, Rotation, Cropping, Scaling, Shearing, Jittering, Stretching, Blurring, Sharpening, Histogram Modification, Restoration, and Noise addition.

14. The CAD method of claim 9, further comprising:
classifying the at least one ROI on the gaze area.

15. The CAD method of claim 9, further comprising:
displaying the modified first detection result of the at least one ROI on the medical image.

16. The CAD method of claim 9, wherein the modifying comprises:
determining whether an ROI on the medical image with respect to the gaze area is one among a false positive, a false negative, and a true positive, based on the at least one ROI on the gaze area;
in response to the determining that the at least one ROI on the medical image with respect to the gaze area is the false positive, removing a marker for the at least one ROI on the medical image with respect to the gaze area;
in response to the determining that the at least one ROI on the medical image with respect to the gaze area is the false negative, adding the marker for the at least one ROI on the medical image with respect to the gaze area; and
in response to the determining that the at least one ROI on the medical image with respect to the gaze area is the true positive, maintaining the marker for the at least one ROI on the medical image with respect to the gaze area.

* * * * *